United States Patent [19]

Pezzulla

[11] Patent Number: Plant 5,812

[45] Date of Patent: Nov. 25, 1986

[54] TOMATO PLANT 'PEZZULLA'

[76] Inventor: Anna M. Pezzulla, P.O. Box 207, Morrisdale, Pa. 16858

[21] Appl. No.: 627,900

[22] Filed: Jul. 5, 1984

[51] Int. Cl.[3] ..... A01H 5/00

[52] U.S. Cl. ..... Plt./89

[58] Field of Search ..... Plt./89

*Primary Examiner*—James R. Feyrer

*Attorney, Agent, or Firm*—Steel, Gould & Fried

[57] ABSTRACT

A new and distinct variety of paste-type tomato is derived in part from the "Roma" and in part from Italian banana tomatoes. The plant is characterized by thick stalks and stems, but slender, relatively-sparce light green foliage. The plant flowers early, and sets long, thin blossoms. Maturity is reached in approximately seventy-eight days. Very numerous, uniformly large, low acid fruit are produced in clusters of five or six fruits per cluster and more than thirty fruits per plant. The fruits are meaty and have few seeds. The fruits are extremely large, weighing one to three pounds, and measure twelve to seventeen centimeters in length and five to eight centimeters in diameter in an elongated plum shape.

9 Drawing Figures

The present development is a new and distinct tomato plant which is a selection taken from plants which are believed to have been second back crosses to the current "Roma VF" from an initial cross between "Roma VF" (pollen parent) X "Italian Banana" (seed parent). Seeds from the initial cross were grown out and observed to develop into plants of varied intermediate types. Selection from the $F_1$ generation was on the basis of size and abundance of fruit with fruit shape not being a critical selection factor. Seed from selected plants was then planted in close proximity to "Roma VF". In the generation which followed, selection was again based on fruit size and abundance. Seed of the second selection was again planted in close proximity to "Roma VF". Selection from the last named generation was based on fruit size and abundance as well as plant vigor. The instant plant is a selection taken from plants grown from seeds of the last named generation.

The original plant parent (Italian Banana) was a producer of a few large short stocky fruits but most were long and very slender, curved somewhat in the shape of a letter "J" or banana as the name implies, with a very pronounced nipple (portion of decreased diameter) at the blossom end of the fruit on indeterminate plants. The pollen plant parent was the Roma VF which was characterized by very uniform, small fruit on determinate plants. The blossoms of the instant plant are much larger and longer than either parent, and developed into much larger and more uniform tomatoes. The shape of the fruit of my tomato plant most nearly resembles the shape of "Roma VF" (but larger), apparently due to the respective back-crosses of respective selections thereto. This new variety has taken on a uniform fruit character, and increased fruit per cluster, but not as many in a cluster as pollen parent Roma VF. The fruit shape is somewhat similar to the Roma VF, only 10 to 15 times larger. This new variety has more seeds than the original plant parent (Italian Banana) which characteristic may be closer to the pollen parent (Roma VF), but has maintained the thick meaty texture and very small seed cavity of the female parent. The seed cavity has increased in size to accommodate the increase in seeds but the fruit is also much larger). This tomato is also a very tasty eating tomato, especially appropriate for people with low acidity diets or for easy removal of seeds as required by people with colon trouble.

The resulting plant is characterized by features which distinguish it from both parents, which features are not true and established, and characterize successive generations. The resulting plant, being hereby named the "Pezzulla," is also distinguished from all other tomato varieties of which I am aware, by virtue of a number of outstanding characteristics, including the following:

(1) The plants produce a thick stalk and relatively thick stems as compared to the Roma VF and Italian Banana varieties. The Roma VF is a determinate tomato and was pollen parent. The Pezzulla is an indeterminate tomato as was the Italian Banana female parent. The foliage is relatively sparse and lighter green in color than that of the Roma VF. Leaves are slender and fine.

(2) The plants begin to blossom early in the season and continue until frost. Individual blossoms are long and slender, measuring up to an inch in length.

(3) The plants are not particularly bushy. If staked, the plants will grow to an indeterminate length of approximately six feet, given the typical growing seasons of central Pennsylvania.

(4) The plants are remarkably resistant to drought, and continue during dry periods to produce large numbers of large fruit. The plant reaches maturity in about seventy-eight days, and will thereafter continue to produce fruit until frost, approximately ninety days thereafter in the area where developed. The fruits are uniformly large and appear in clusters of five to six fruit per cluster, each plant having five to six clusters. The fruits are much larger than would be expected from the fruit of either the Roma VF or Banana parents, each fruit weighing from one to three pounds and measuring twelve to seventeen centimeters, whereas, the Roma VF tomato weighs about two and one-half ounces and is approximately six to seven centimeters in length. The Pezzullas tomatoes are very long, very large, stocky elongated plum-shaped fruit varying somewhat to tapering or teardropped shape with a short conical nipple.

(5) The fruits are low in acid and have a very meaty texture and sweet taste.

(6) The Roma's resistance to verticillium and fusarium wilts appears to have been maintained.

(7) Asexual reproduction of the new Pezzulla variety, accomplished by rooting cuttings, shows that the characteristics of the plant are fixed and appear in succeeding generations.

(8) The seeds are very small (much smaller than the pollen parent Roma VF), but the germination rate is 95% to 100%.

The accompanying photographs show a number of specimens of the plant and its blossoms and fruit, throughout various stages of growth, as experienced in the summer of 1983 in central Pennsylvania. The plants shown in the drawings were neither staked nor watered (except by natural rainfall) for the entire growing season. The resulting plants and their production was far superior to that of any variety of this type known to the applicant.

The following outline sets forth a number of distinguishing features over plants known before and may be compared to photographs of the plant as attached hereto. Color specifications mentioned herein were determined by reference to The Royal Horticultural Society Colour Chart (R.H.S.) published by The Royal Horticultural Society of London, England.

The Plant

Type: Paste-type tomato of indeterminate habit bearing extremely large and numerous fruit.

Breeding and propagation: Developed initially by accidental cross-breeding of Roma VF and Banana varieties, and thereafter, by deliberately selecting of the most desirable characteristics and successive backcrosses with Roma VF. Resulting plant holds its distinguishing characteristics through succeeding propagations by rooting of cuttings.

Habit and average height and spread: Bushiness as shown is due to the numerous branches, the nodes occurring every 2–3 inches, although individual leaves are relatively slender and fine.

Growth: Average rate of growth reaching an indeterminate height of approximately six feet if staked.

Foliage: Leaves are relatively thin and fine, and appear in compound groups of five, seven or nine. Frequently, a compound of seven leaves is interspersed with smaller, relatively round leaflets between the larger leaflets which are included in the defined compound. The leaflets are long and narrow which uneven serrations along the leaf margin. The leaves are thinner than that of the Roma VF variety, and of equal or longer length. Mature leaflets are about 2–3 inches in width tapering evenly to a point. The length of the mature leaflet is about 4–6 inches. Leaf color is green (143A).

Stems and branches: The plants produce a thick stalk having closely-spaced stems. The stems are thicker than either parent. Branches and new stems are also relatively thick and short.

Flowers: Flowers appear in clusters of five or six on a flower stem which is also relatively long and thick. Individual flowers are quite long and thin, measuring up to an inch in length. The sepals have slender points which extend nearly perpendicularly outwards from the flower as the blossom matures. Blossom color is yellow (15A) at flower center and outer flower petal color is yellow (5B.)

The Fruit

Bearing: Quite heavy, more than thirty fruits per plant.

Shape: Very long, very large, stocky elongated plum-shaped fruit varying somewhat to tapering or teardropped shape with a short conical nipple.

Size: Quite heavy, ranging from one to three pounds and measuring up to seventeen centimeters in length and ten centimeters in diameter. Average weight is two pounds. Length ranges from twelve to seventeen centimeters, averaging fifteen centimeters and width ranges from eight to ten centimeters, averaging nine centimeters.

Texture: Very meaty and having few seeds. The fruit locules are relatively small in volume and are confined primarily to the area adjacent to the inner surface of the external wall of the fruit.

Color: External color is deep red (42B).

Season: First fruits mature about seventy-eight days after plants are set out, depending upon conditions. Plants then bear fruit until frost, resulting in a season of about ninety days, as experienced in central Pennsylvania.

Flavor: Sweet taste and low in acid.

Skin: Characterized by thin walls and not prone to cracking.

Disease resistance: Has field tolerance to verticillium and fusarium wilt comparable with the Roma VF variety.

Drought resistance: Outstanding drought resistance.

What is claimed is:

1. A new and distinct variety of paste-type tomato plant, as described and illustrated, characterized by a thick stalk and closely-spaced stems, and slender, light green, relatively sparse leaves, long, thin clustered blossoms developing into very numerous, very uniform and very large stocky, elongated plum-shaped fruit varying somewhat to tapering or teardropped shape with a short conical nipple, the fruits being very meaty and with few seeds, the overall plant being quite hearty and drought resistant.

* * * * *

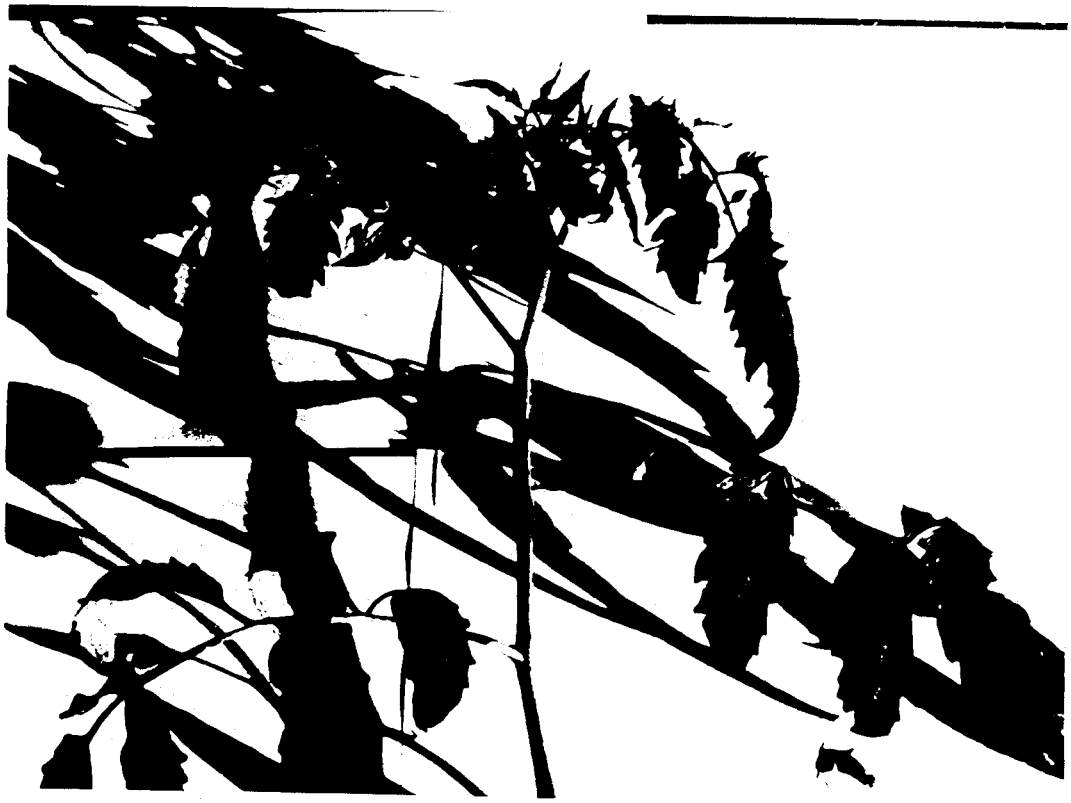
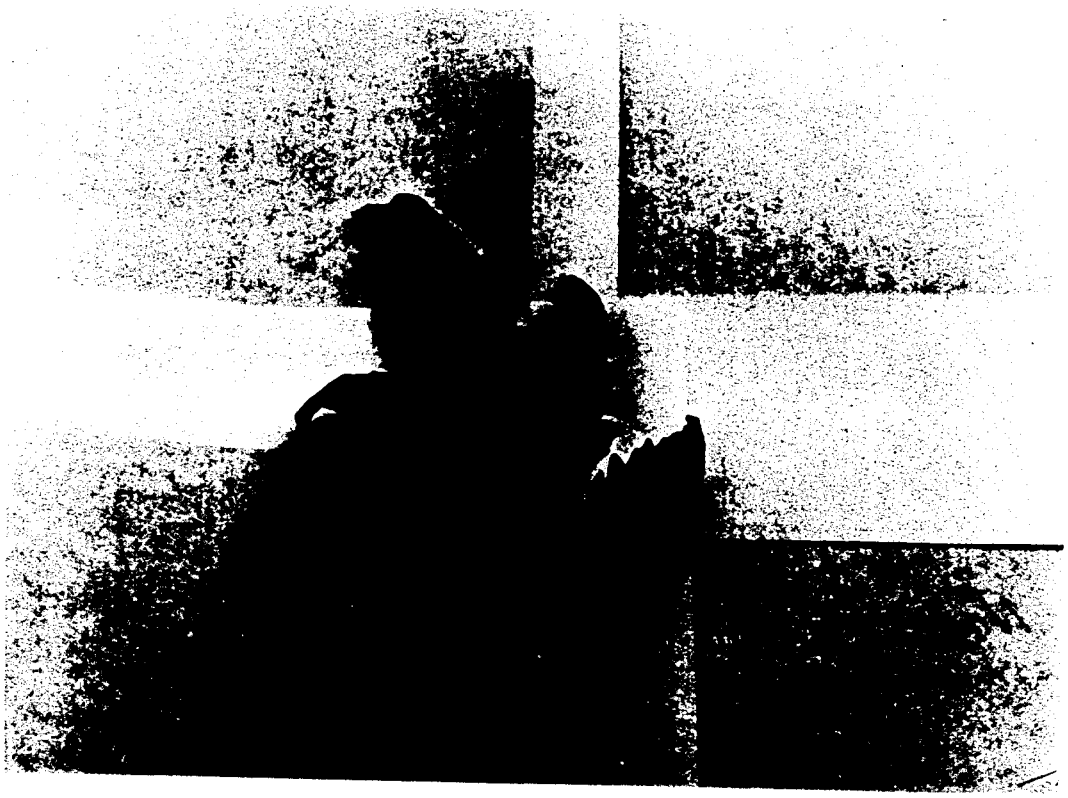

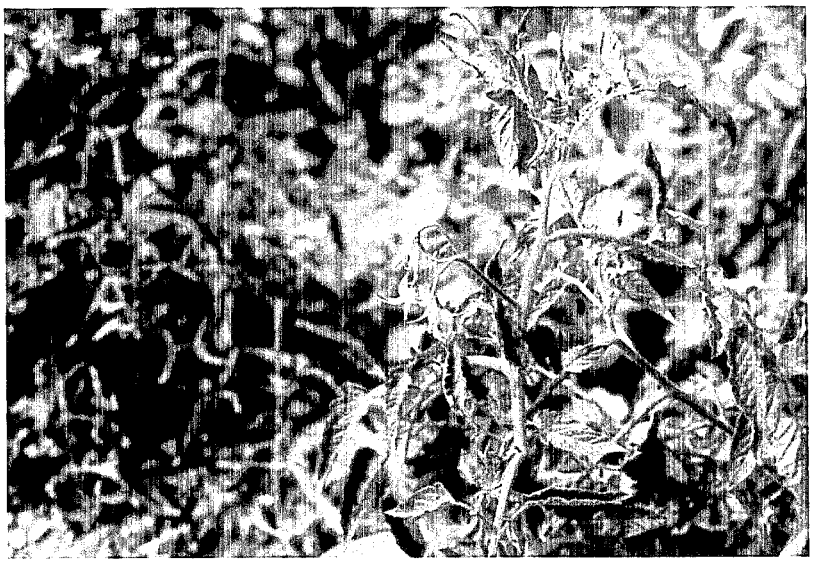
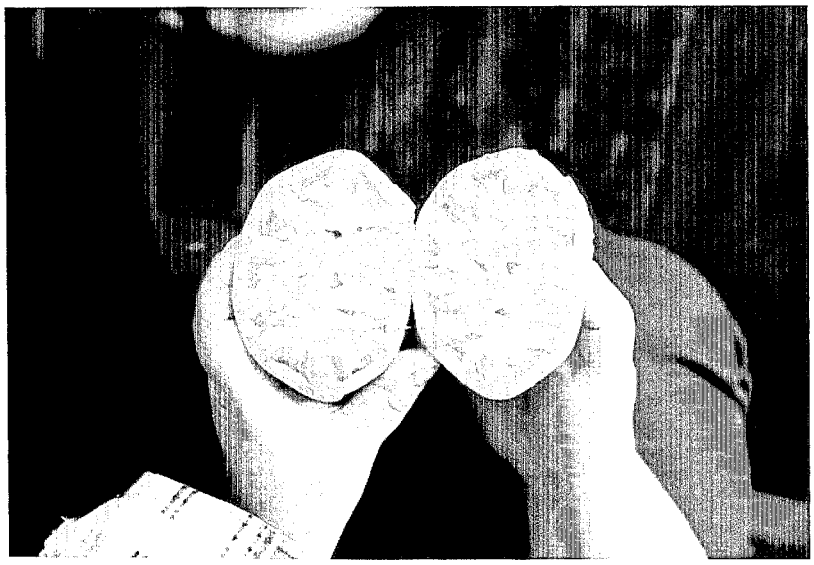

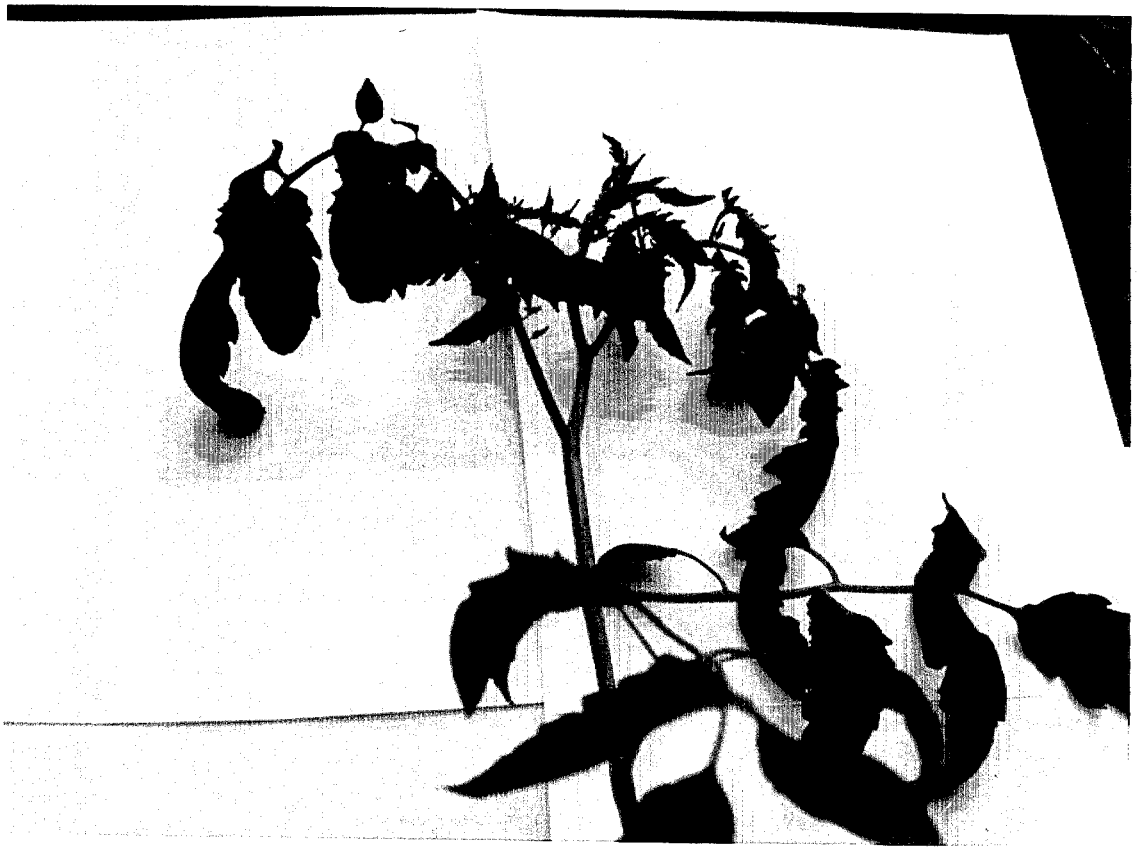

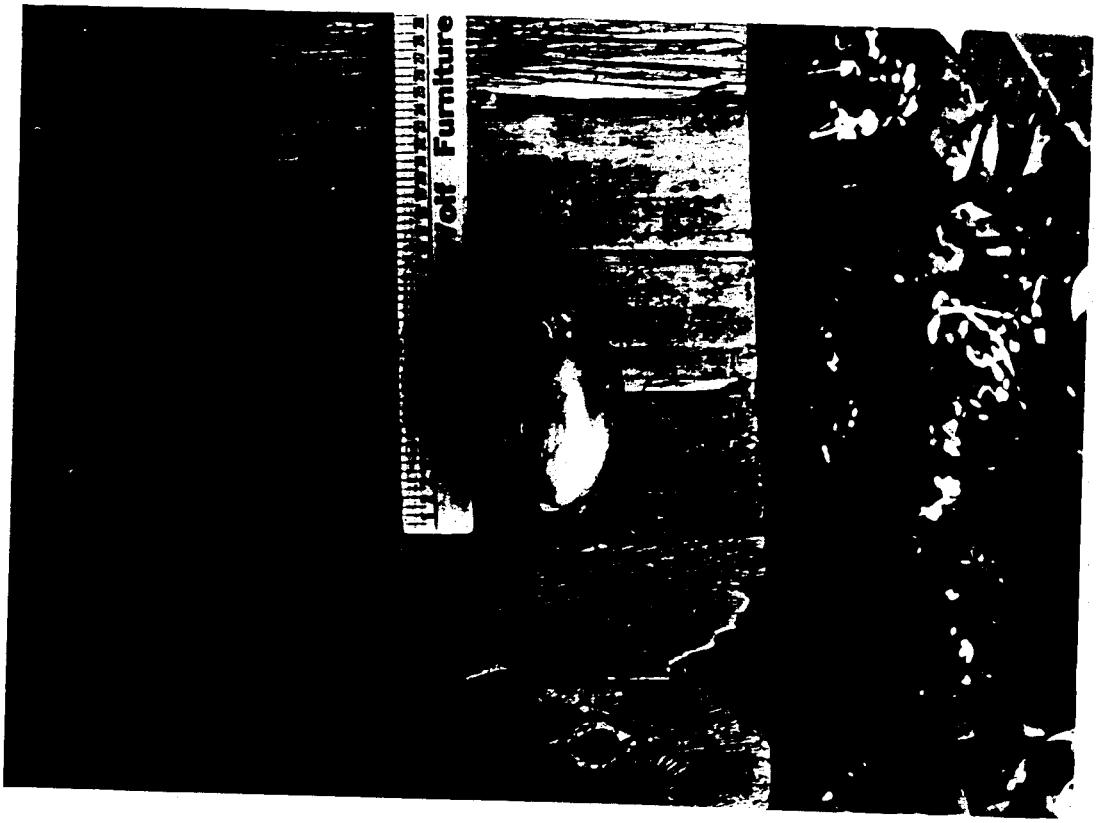
Soft Furniture
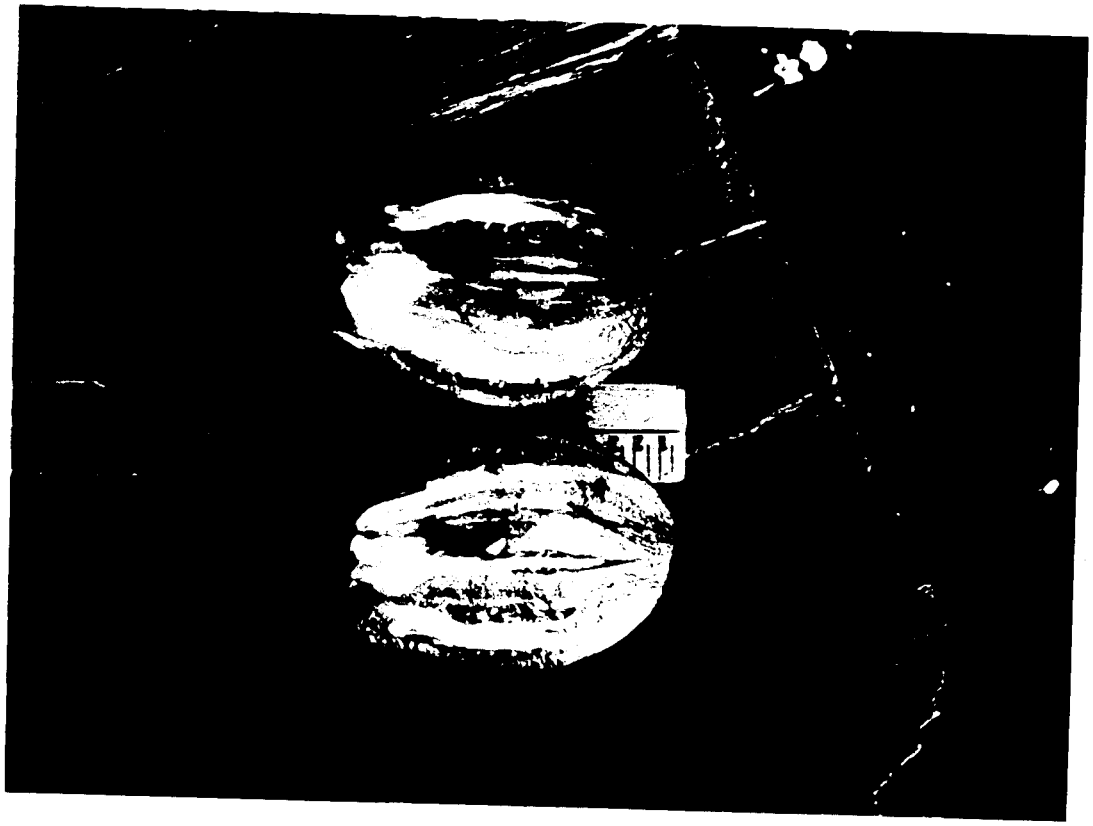

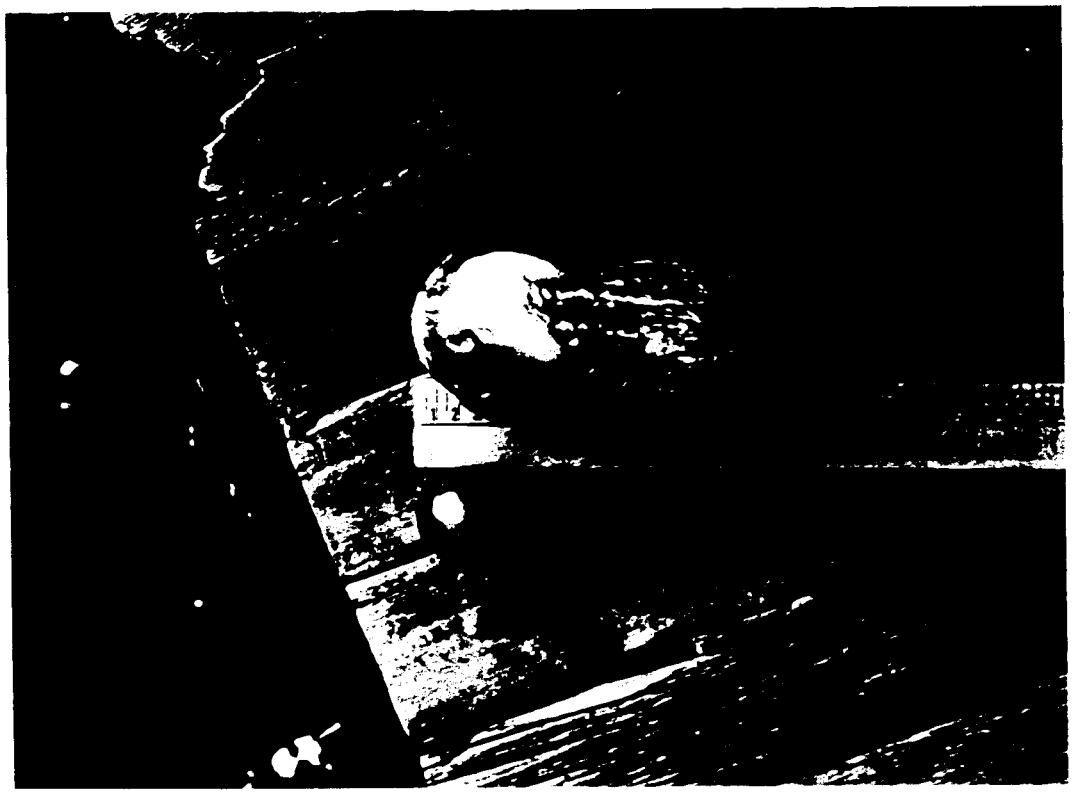

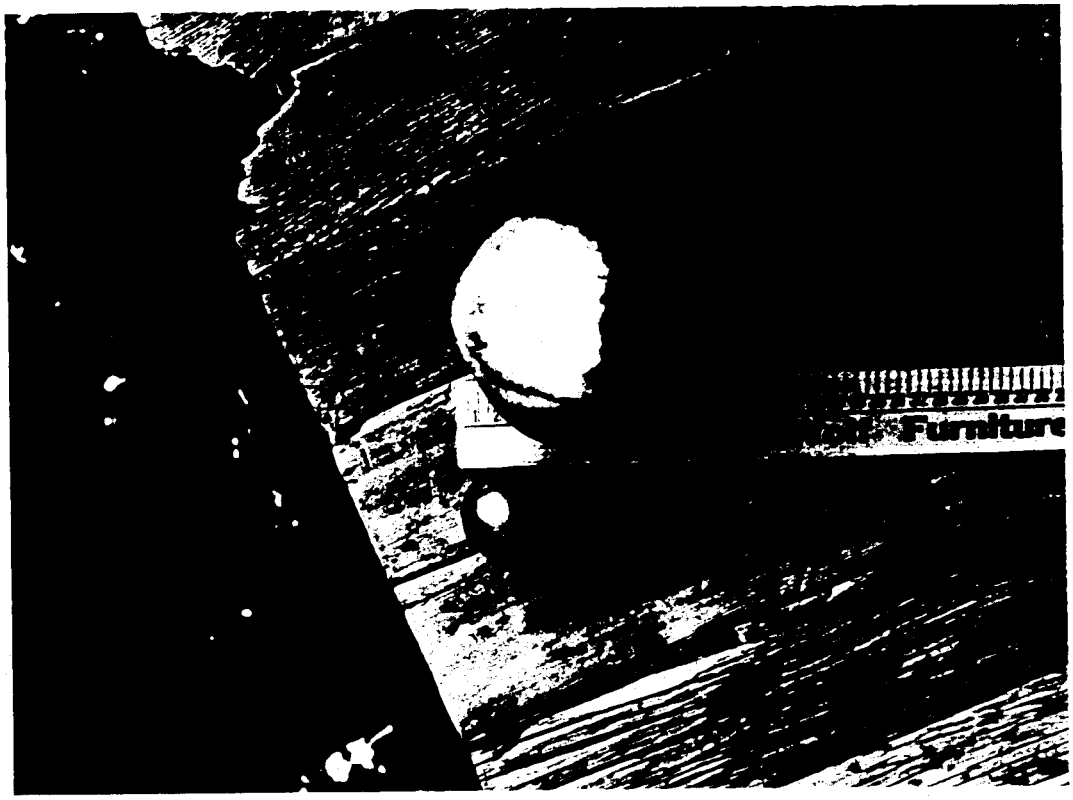
Furniture